(12) United States Patent
Antila et al.

(10) Patent No.: US 9,772,228 B2
(45) Date of Patent: Sep. 26, 2017

(54) DEVICE AND METHOD FOR OPTICAL MEASUREMENT OF A TARGET

(71) Applicant: TEKNOLOGIAN TUTKIMUSKESKUS VTT, Vtt (FI)

(72) Inventors: Jarkko Antila, Helsinki (FI); Jussi Tenhunen, Kiiminki (FI)

(73) Assignee: TEKNOLOGIAN TUTKIMUSKESKUS VTT OY, Espoo (FI)

( * ) Notice: Subject to any disclaimer, the term of this patent is extended or adjusted under 35 U.S.C. 154(b) by 0 days.

(21) Appl. No.: 15/030,697

(22) PCT Filed: Oct. 21, 2014

(86) PCT No.: PCT/FI2014/050791
§ 371 (c)(1),
(2) Date: Apr. 20, 2016

(87) PCT Pub. No.: WO2015/059353
PCT Pub. Date: Apr. 30, 2015

(65) Prior Publication Data
US 2016/0252394 A1 Sep. 1, 2016

(30) Foreign Application Priority Data
Oct. 21, 2013 (FI) .................................. 20136036

(51) Int. Cl.
*G01B 9/02* (2006.01)
*G01J 3/26* (2006.01)
(Continued)

(52) U.S. Cl.
CPC . *G01J 3/26* (2013.01); *G01J 3/44* (2013.01); *G01N 21/65* (2013.01); *G02B 5/28* (2013.01); *G02B 26/00* (2013.01)

(58) Field of Classification Search
CPC .. G01J 3/26; G01J 9/0246; G01B 9/02; G02B 26/001; G02B 6/29358
See application file for complete search history.

(56) References Cited

U.S. PATENT DOCUMENTS

| 3,723,007 A | 3/1973 | Leonard |
| 4,365,153 A | 12/1982 | Seigel et al. |

(Continued)

FOREIGN PATENT DOCUMENTS

| EP | 0 543 578 A1 | 5/1993 |
| WO | 9425861 A1 | 11/1994 |
| WO | 2010/112679 A1 | 10/2010 |

OTHER PUBLICATIONS

International Search Report, dated Feb. 27, 2015, from corresponding PCT application.
(Continued)

*Primary Examiner* — Tarifur Chowdhury
*Assistant Examiner* — Md M Rahman
(74) *Attorney, Agent, or Firm* — Robert P. Michal, Esq.; Carter, DeLuca, Farrell & Schmidt, LLP

(57) ABSTRACT

A device and a method for optical measurement of a target, wherein the target is irradiated with radiation beam (15) and a measurement beam (27) is received from the target and detected. Commonly used absorbance, reflectance and fluorescence measurements do not provide adequate information in e.g. measuring small contents of sulphur compounds. The present solution provides a new Raman spectrometer which is suitable for mass applications. A target is activated with pulses of a laser diode (12). The Raman signatures are measured and integrated successively with a point detector (44). A Fabry-Perot interferometer (42) on the measurement path is successively controlled into corresponding pass bands. While high spectral resolution or range is not
(Continued)

Figure 1:
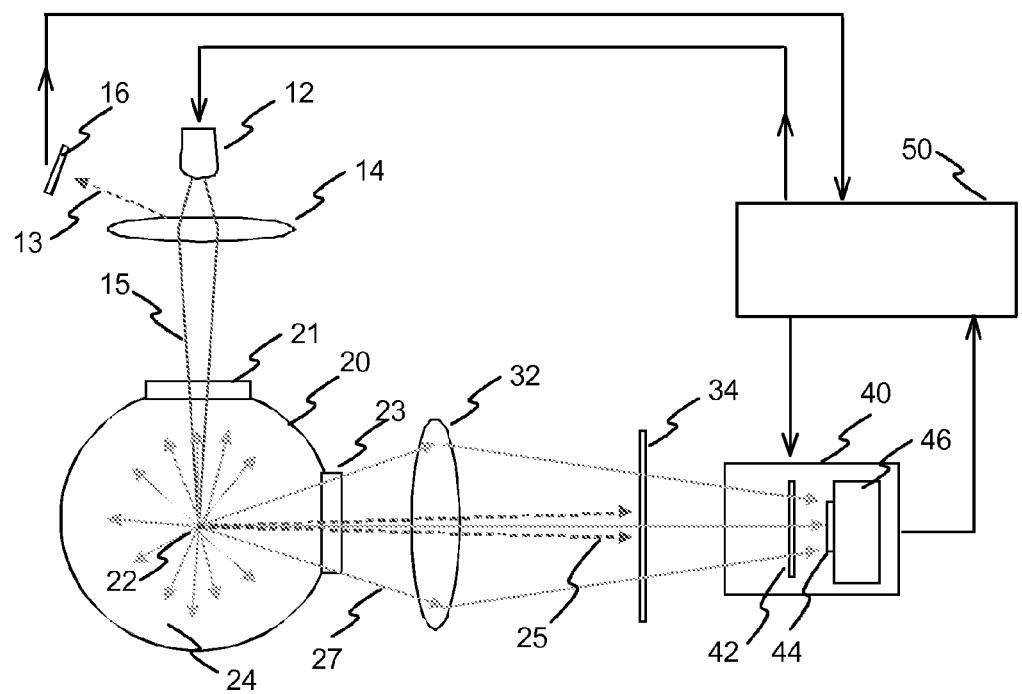

required it is possible to use small-sized and low cost components.

13 Claims, 2 Drawing Sheets

(51) Int. Cl.
*G01J 3/44* (2006.01)
*G01N 21/65* (2006.01)
*G02B 5/28* (2006.01)
*G02B 26/00* (2006.01)

(56) References Cited

U.S. PATENT DOCUMENTS

| 2005/0264808 | A1 | 12/2005 | Wang | |
|---|---|---|---|---|
| 2007/0133984 | A1* | 6/2007 | Maier | G01J 3/28 398/26 |
| 2010/0097613 | A1* | 4/2010 | Saari | G01J 3/10 356/454 |
| 2011/0122407 | A1* | 5/2011 | Jalali | G01N 21/65 356/301 |
| 2012/0038928 | A1* | 2/2012 | Saari | G01J 3/02 356/454 |
| 2012/0203114 | A1 | 8/2012 | Bechtel et al. | |

OTHER PUBLICATIONS

FI Search Report, dated Jul. 30, 2014, from corresponding FI application.

\* cited by examiner

DEVICE AND METHOD FOR OPTICAL MEASUREMENT OF A TARGET

TECHNICAL FIELD

The invention relates to a device and a method for optical measurement of a target, wherein the target is irradiated with radiation beam and a measurement beam is received from the target and detected.

BACKGROUND TECHNOLOGY

Optical measurement systems are used for e.g. analysing properties or material contents of a target. The most common optical measurement devices are based on light absorbance/reflection of a target or fluorescence of a target. Such measurements are needed in laboratories and industry, for example. However, there is also a growing need for continuous monitoring of material contents in mass applications, i.e. in applications where a large number of devices are needed and low cost of the devices is important. One such application is monitoring the contents of sulphur in various processes, and especially monitoring contents of sulphur compounds and additives in fuel of a vehicle.

There are some disadvantages related to using prior art technology for monitoring material contents in mass applications, such as the monitoring contents of sulphur. The measurement of absorbance, reflectance and fluorescence are suitable only for certain materials. In measuring contents of sulphur compounds, for example, also the contents to be measured are very low, such as a few ppm. As a consequence, those methods do not provide adequate information on sulphur contents.

One method to solve this problem can be Raman spectroscopy. In Raman scattering phenomenon, upon collision with a molecule a photon loses some of its energy (Stokes radiation) or gains some energy (anti-Stokes radiation). In consequence, the radiation scattered from the molecules of material has a wavelength which is shifted from the wavelength of the initial radiation used for activation. The wavelengths of the scattered radiation are characteristic to a molecule, and they can be called Raman "signatures" of the molecule. For example, there are several signature bands in MIR (middle infrared) region representing sulphur bonds e.g. with coal. With Raman spectroscopy it is thus possible to get information on contents and types of molecules which include sulphur.

Prior art Raman spectrometers are suitable for laboratories, but there are some problems in using them in mass applications like the measurement of sulphur from fuel. Such Raman spectrometers are usually equipped with a high-power narrow-band laser source, a volume holographic grating for achieving high diffraction efficiency, heavily cooled CCD (Charge Coupled Device) camera or array, and a fibre-connected measurement probe with a beam splitter and filters. Such Raman spectrograph instruments provide simultaneous measurement of radiation within a large range of wavelengths and high spectral resolution, such as 4 cm$^{-1}$. However, the instrument is very large-sized and expensive, and it is therefore not suitable for mass applications. Due to the low intensity of the Raman scattered signal and high spectral resolution of the spectrometer the measurement also tends to take a long time in order to achieve a sufficient signal-to-noise ratio.

SUMMARY OF THE INVENTION

The purpose of the present invention is to avoid or reduce disadvantages of the prior art.

The objective of the invention is achieved with a solution, in which a controllable Fabry-Perot interferometer and a point detector are used. The Fabry-Perot interferometer is used for selecting one signature wavelength to be measured at a time. The signatures of the material are detected and integrated sequentially by controlling the Fabry-Perot interferometer into the corresponding pass bands of the signature wavelengths. The measurement device may have low resolution and preferably small size.

More particularly, a device according to the invention for optical measurement of a target, the device comprising a radiation source for providing an activation radiation beam to the target, a detector for receiving measurement radiation beam from the target and providing a signal which corresponds to the amount of radiation received to the detector from the target, and at least one Fabry-Perot interferometer within the path of the measurement radiation beam, is characterised in that the radiation source is a laser radiation source with a substantially fixed radiation wavelength,
the detector is a single point detector,
the Fabry-Perot interferometer has a controllable pass band wavelength,
the device has means for controlling the Fabry-Perot interferometer sequentially into pass bands which correspond to the signature wavelengths of the measured target material,
the device has means for integrating the received measurement radiation signals of each measured signature wavelength, and
the device has means for providing a measurement result on the basis of the integrated signals.

A method according to the invention for optical measurement of a target, comprising providing a radiation beam to the target, receiving measurement radiation beam from the target and providing a signal which corresponds to the amount of radiation received to a detector from the target, and filtering the received measurement radiation beam with a Fabry-Perot interferometer, is characterised in that a laser beam with a substantially fixed radiation wavelength is provided as the radiation beam,
the measurement radiation beam is detected with a single point detector,
the Fabry-Perot interferometer has a controllable pass band wavelength,
the pass band wavelength of the Fabry-Perot interferometer is controlled sequentially into pass bands which correspond to the signature wavelengths of the measured target material,
the received measurement radiation signals of each measured signature wavelength are integrated, and
a measurement result is provided on the basis of the integrated signals.

Some preferable embodiments of the invention are described in the dependent claims.

In one embodiment the point detector is a semiconductor photo detector, and in some embodiments the radiation source for activation is a laser diode.

In a preferable embodiment the integration of radiation is made in the detector by accumulating charges. However, it is also possible to integrate the signals after receiving from the photo detector. In a further embodiment the radiation measurement signals of each signature are integrated separately in order to achieve measurement results for each signature. However, it is alternatively also possible to integrate charges of two or several signatures if separate measurement results for each signature are not needed.

In one further embodiment the spectral points to be measured and the integration times per each spectral point are selected on the basis of the characteristic Raman spectrum of the material to be measured. The measurement points and integration times preferably imitate the Raman spectrum of the measured target material. Measured radiation on these spectral points can be cumulatively integrated and thus one measurement value is achieved instead of spectrum data. A general principle of such matched filtering is described in publication WO2010/112679 of the present applicant.

According to one embodiment the device is primarily designed for measuring only contents of molecules which have a predetermined chemical element, such as sulphur.

According to a further embodiment the device comprises a fixed filter within the path of the measurement radiation beam, which fixed filter is arranged to block radiation with the wavelength of the radiation source and/or other than Raman emission received from the target or environment. The fixed filter may include a single filter or a set of filters. It may include band pass, low pass, high pass and/or notch filters, for example. In one further embodiment there is also a filter in the path of the activation beam of the radiation source. Such a filter may be a fixed pass band filter, for example, for blocking any disturbing radiation from entering measurement space.

It is possible to achieve substantial advantages with the present invention, such as very high signal-to-noise ratio. It is possible to measure contents of sulphur and many other chemical elements, which cannot be adequately measured with other common methods. The device is relatively efficient because a laser diode may give a short pulse with high momentary power, and a point detector may receive all available measurement radiation and provide a signal which corresponds to the total amount of gathered radiation. The sensor area of the point detector may also have a large size to maximize the detected radiation. Matched bandwidths of the source and the filter can be used. It is also possible to use a vertically controllable Fabry-Perot interferometer, which has a large aperture compared to interferometers that have planarly moving structures. It is not necessary to have a slit in the measurement path or small pixels which would decrease the signal-to-noise ratio as required in prior art grating spectrometers.

When a single chemical element is measured it is also sufficient to have low spectral resolution, such as $\geq 85$ cm$^{-1}$. For these reasons it possible to achieve a good signal-to-noise ratio in the signal detection, even without heavy cooling of the detector. Due to low resolution it is not possible to achieve accurate line detection, but when the configuration is used as a sensor for a limited matrix, such as fuel, then chemometric tools can be applied to achieve required information on the material based on the measurement.

It is possible to achieve a moderate cost for a device because mass production components can be used. When only low resolution is required it is possible to use low-cost laser diodes as a laser source, which are typically used in automotive or telecom applications. Also, only one low-cost single point detector is required.

It is also possible to provide a measurement device in a very small space because large-sized components are not needed. A size of a Fabry-Perot interferometer is not larger than any other optical components, such as lenses, which are used in small-sized optical equipment. A device according to the invention can also be made robust, because mechanically sensitive components are not needed. Also, because there is no need for high power radiation source or high requirement for cooling a detector, the power consumption of the measurement equipment can be made small.

It is possible to use NIR (Near Infrared Range) wavelengths with the present low-cost arrangement, and to avoid the problems of background fluorescence.

In this patent application the term "Fabry-Perot interferometer" means a component with at least two reflecting surfaces which cause an interference effect when illuminated with radiation. The pass band of a Fabry-Perot interferometer is preferably electrically controllable. The pass band may relate to transmitted and/or reflected radiation of a Fabry-Perot interferometer.

In this patent application the terms "radiation" or "light" are used to mean any radiction in the optical range of wavelengths.

In this patent application the term "fixed filter" means an optical filter which does not have an electrically controllable pass band.

SHORT DESCRIPTION OF THE DRAWINGS

Figure 2:
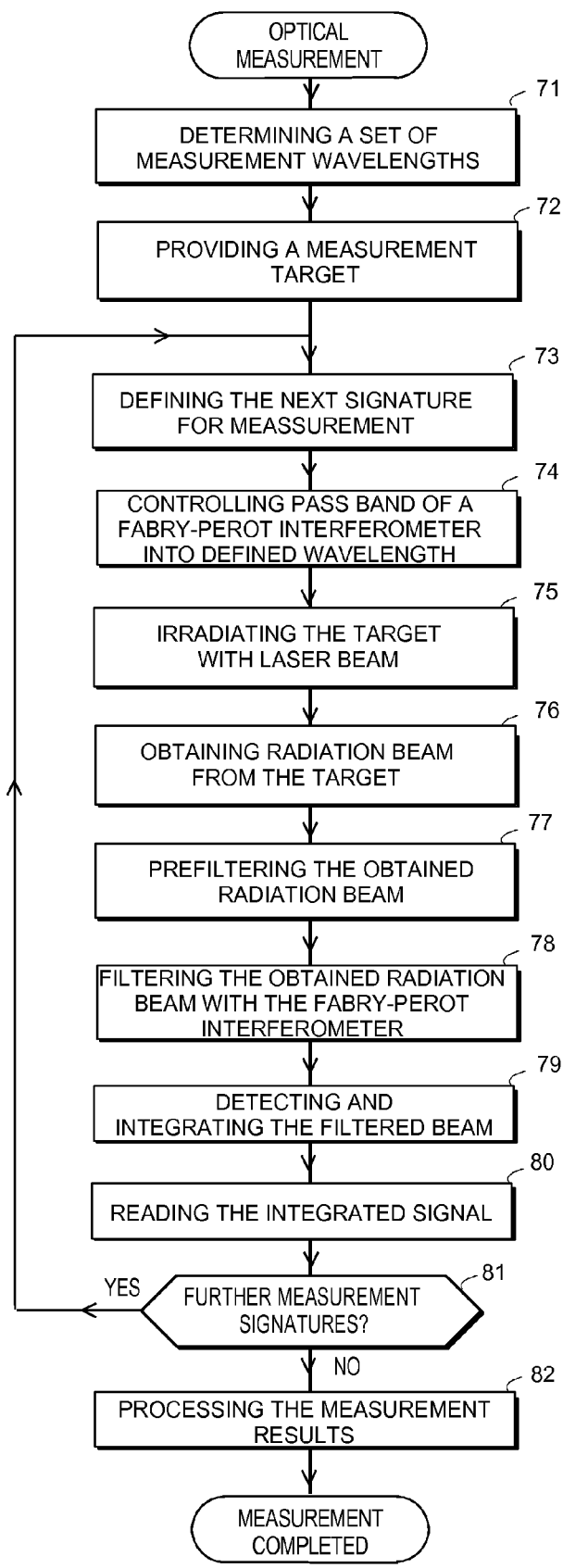

In the following part the preferable exemplary embodiments of the invention are described in more detail by referring to the enclosed drawings, in which:

FIG. 1 illustrates a block diagram of an exemplary optical measurement device according to the invention; and FIG. 2 illustrates a flow diagram of an exemplary method for providing an optical measurement according to the invention.

DETAILED DESCRIPTION OF EMBODIMENTS

FIG. 1 illustrates an exemplary measurement device according to the invention. The device has a laser radiation source 12. The radiation source is preferably a laser diode. The output optical power can be e.g. within range 5-50 W, such as 20 W. The radiation source is controlled with control means, such as a microcontroller 50. The radiation beam 15 of the radiation source is focused into a measurement point 22 with a lens 14. There may also be a filter (not shown in FIG. 1) within the path of the activation radiation beam. A filter can be used for blocking possible disturbing radiation on other wavelengths from reaching the measurement space. The device may also have a separate photo detector 16 for monitoring the intensity of the radiation provided by the radiation source. The photo detector 16 may measure radiation 13 reflected from the lens 14, for example. The measurement of the radiation output can be used as a feedback by the control means 50 in controlling the laser diode to achieve correct radiation intensity.

The measurement device has a space for the material to be measured. In the case of FIG. 1 this measurement space is inside a tube 22, and FIG. 1 shows the cross section of the tube. Inside the tube there is flowing fuel, which is measured for its contents of sulphur compounds. The tube has an entrance window 21 for transmission of the radiation from the radiation source. The radiation received from the laser diode causes Raman scattering in the measurement point 22. In the Figure, the measurement point 22 is located in the middle of the tube 20, but the measurement point may locate in some other alternative location within the measurement space.

The tube may also have a reflective inner surface, which causes the radiation beam of the laser source to reflect from the inner surfaces of the tube. This enhances the radiation intensity at the measurement point and thus increases the amount of Raman scattered measurement radiation. The Raman scattered radiation is also reflected from the inner surface of the tube, and a larger proportion of the measurement beam is also received for detection. When a reflecting inner surface is used it is preferable to have a small angle between the radiation beam of the radiation source and the measurement beam received by the detector. The angle in the device of FIG. 1 is 90 degrees which is considered suitable. However, it is also possible to use a same window for both the radiation beam and the measurement beam. In such an arrangement a beam splitter can be used for separating the beams.

In the arrangement of FIG. 1 the tube 20 has another window 23 for transmitting the Raman scattered measurement beam 27. Some reflected radiation 25 without Raman scattering is also received from the measurement space. The received measurement radiation beam is gathered and focused with lens 32 to the point detector 44. Before entering the photo detector the measurement beam is filtered. Filter 34 may be a set of fixed wavelength notch filters, high pass filters and low pass filters, for example, filtering out disturbing radiation such as non-scattered radiation of the radiation source and radiation from fluorescence emissions. The high pass and low pass filters may determine the overall measurement range of the device. The measurement beam is further filtered with a controllable Fabry-Perot interferometer 42. The Fabry-Perot interferometer is controlled by a micro-controller 50 into a pass band which corresponds to a signature wavelength of the material being measured. Thus radiation of the signature wavelength substantially passes the filters 34, 42 and enters the photo detector 44, while disturbing radiation and signatures with other wavelengths are substantially blocked by the filters.

The point detector 44 is a semiconductor photo detector, such as an InGaAs detector, which has a cooling element 46 providing moderate cooling for the photo detector. The photo diode, the cooling element and the Fabry-Perot interferometer are preferably integrated into a single component 40. The Fabry-Perot interferometer is preferably produced by MEMS technology. MEMS technology allows integration of the Fabry-Perot interferometer with a photo detector. However, it is also possible to use another type of a Fabry-Perot interferometer, such as one based on piezoelectric actuators, which has better filtering characteristics but which is larger and more expensive to produce.

The photo detector converts the received radiation into an electric charge, which is read by the microcontroller 50 as an electrical signal. Usually there are several Raman signatures that are measured from the material. The measurement of different signatures is made successively, i.e. the Fabry-Perot interferometer is controlled successively into pass bands that correspond to the signatures, which are measured. After collecting beams of a signature and integrating the charges, the photo detector is read by the microcontroller. The Fabry-Perot interferometer is then controlled into a pass band that corresponds to the next signature, and the corresponding radiation is detected. FIG. 2 shows the measurement process in more detail.

Next characteristics of an exemplary device according to FIG. 1 is described. The wavelength of the activation radiation from the radiation source is selected on the basis of the Raman range of the material to be measured, suitable spectral range of a detector, and wavelengths of expected fluorescence. The probability of Raman scattering increases with wave number of the activation radiation. Disturbing fluorescence emissions may originate from the material to be measured and the materials of the measurement device. In order to avoid disturbing radiation of fluorescence emissions, it is preferable to select such Raman operating wavelength range where the fluorescence emissions are minimal. It is also possible to use fast pulsed time-gating in the measurement so that the measurements of the Raman scattering are made before fluorescence emissions start, and the next measurement period begins after the fluorescence emission has finished.

If an InGaAs detector is used the spectral response is between 1200-1600 nm together with a Fabry-Perot interferometer. When the wave numbers of the desired Raman signatures are between 1000 and 1500 $cm^{-1}$ this yields that the minimum excitation number is 7250 $cm^{-1}$ and the maximum wave number is 9833 $cm^{-1}$, which correspond to wave lengths 1379 nm and 1017 nm, respectively. For example, an Nd:YAG laser with radiation wave length of 1064 nm can be used as a radiation source. The achieved Raman range is in this case 1065 $cm^{-1}$-3148 $cm^{-1}$.

If the Raman vibration line is sharp, the spectral resolution of the measurement depends on the characteristics of the radiation source that is used for activation. When an InGaAs laser diode is used, a peak output optical power may be 20 W, whereby Raman power will be approx. 1 µW. Pulse duration may be 100 ns maximum, and the duty cycle may be 0,1% maximum. A typical wavelength is 905 nm. This yields that FWHM (Full Width at Half Maximum) is 7 nm, which corresponds to the spectral resolution of 85 $cm^{-1}$. When the resolution of the Fabry-Perot interferometer is matched to this value the resolution of the Fabry-Perot interferometer must be 12 nm at 1200 nm operation wavelength and 22 nm at 1600 nm operation wavelength.

FIG. 2 illustrates a flow diagram of an optical measurement method according to the invention. First it is determined, which signatures are measured, phase 71. If the measurement device is dedicated to measuring only certain signatures it is possible that the signatures are determined only once for a given device. Next a target is provided into a measurement space for measurement in phase 72. The target may be fuel in a fuel tube or a sample in a sample well, for example. It is then defined, which signature is measured next, phase 73.

After selecting the signature the Fabry-Perot interferometer is controlled to form a pass band which corresponds to the selected signature, phase 74. An activation radiation beam is then directed to the measurement point of the target in phase 75. A Raman scattered measurement beam is thus obtained, phase 76. The measurement beam is optionally pre-filtered with a fixed wavelength filter in order to block disturbing radiation which is not Raman scattered, phase 77. The measurement beam is then further filtered with the Fabry-Perot interferometer which has been controlled to pass the radiation of the selected signature. The Fabry-Perot interferometer blocks the other, non-selected signature beams. It should be noted that the Fabry-Perot interferometer may also locate before the other filter in the path of the measurement beam.

The filtered measurement beam is then received to a point detector. The detector converts the beam into electrical charge, which is integrated, phase 79. The irradiation of the target and detecting the signal of a signature lasts for a defined period of time. When the time has lapsed, the integrated charge of the detector is read by a microcontroller, phase 80. It is then checked in phase 81 whether there are further signatures to be measured. If measurements of further signatures are to be made the process re-enters phase 73. If no other signatures are to be measured the microcontroller calculates to material contents on the basis of the collected signals in phase 82. The information of the material contents/compound types can then be used for required purposes or stored for future use.

A measurement device may be programmed to make continuous measuring, where the device measures defined signatures in succession and repeats this procedure as long as the device is running. If material contents in fuel of a car are monitored, it is possible that the monitoring is performed when the car motor is running, and the measurement is stopped for other times.

In the previous embodiments the signals of each signature were separately integrated. This way it is possible to achieve separate results on the contents of chemical bonds corresponding to each signature. It is also possible that this information is not required, but it is only necessary to get information on the total contents of a certain chemical element. In this case it is possible to integrate the signals from two or several signatures before reading the detector. When several measurement beams are integrated it is possible to increase the signal-to-noise ratio of the measurement. When N signature signals are integrated, the signal is increased by factor N, but the readout noise does not increase. Therefore, it is possible to increase the signal-to-noise ratio more than if each successive signature would be read out separately. As an alternative, it is also possible to use a Fabry-Perot interferometer which has two simultaneous pass bands and which can be controlled to pass beams of two selected signatures simultaneously.

If the target material is transparent for the measurement radiation it is possible to have the measurement point inside the target as shown in FIG. 1. However, the present invention can also be used for measuring materials which are not transparent for the measurement radiation. In such cases the measurement point is located at the surface of the target.

An optical measurement system commonly includes processing means for performing the optical measurement process. The control of the measuring process in an optical measurement instrument generally takes place in an arrangement of processing capacity in the form of microprocessor(s), and memory in the form of memory circuits. Such arrangements are known as such from the technology of analyzers and relating equipment. To convert a known optical instrument into equipment according to the invention it may be necessary, in addition to the hardware modifications, to store into the memory means a set of machine-readable instructions that instruct the microprocessor(s) to perform the operations described above. Composing and storing into memory of such instructions involves known technology which, when combined with the teachings of this patent application, is within the capabilities of a person skilled in the art.

The invention has been described with the reference to the enclosed embodiments. It is, however, clear that the invention is not restricted only to those, but comprises all embodiments which can be imagined within the inventive idea and the enclosed patent claims.

For example, the described applications and targets are exemplary and only serve to assist in understanding the functionality of the invention. It is clear that the invention can be used for measuring different types of targets and contents of different substances where the Raman scattering exists. It is also possible to combine the present device with other types of measurements such as infrared or fluorescence measurements.

The invention claimed is:

1. A device for optical measurement of a target with Raman spectroscopy, the device comprising:
a radiation source for providing an activation radiation beam to the target, a detector for receiving a measurement radiation beam of Raman scattered radiation including signature wavelengths of a measured target material from the target and providing a signal which corresponds to the amount of radiation received by the detector from the target, and a Fabry-Perot interferometer disposed within the path of the measurement radiation beam, wherein:
the radiation source is a laser radiation source with a substantially fixed radiation wavelength,
the detector is a single point detector,
the Fabry-Perot interferometer has a controllable pass band wavelength,
the device is configured to control the Fabry-Perot interferometer sequentially into pass bands which correspond to signature wavelengths of the measured target material,
the device is configured to integrate the received measurement radiation signals of each measured signature wavelength,
the device is configured to provide a measurement result on the basis of the integrated signals
measurement radiation of a plurality of selected wavelengths is successively measured and cumulatively integrated, and
wherein the plurality of selected wavelengths and the integration times per each wavelength point are selected on the basis of the characteristic Raman spectrum of the target material to be measured.

2. The device according to claim 1, wherein the detector is configured to integrate the received measurement radiation signals.

3. The device according to claim 1, wherein the detector is a semiconductor photo detector.

4. The device according to claim 1, wherein the laser radiation source is a laser diode.

5. The device according to claim 1, wherein the device is arranged to integrate the radiation measurement signals of each signature separately.

6. The device according to claim 1, wherein the device is arranged to measure signatures of predetermined molecules which include a predetermined chemical element.

7. The device according to claim 1, wherein the device further comprises a fixed filter within the path of the measurement radiation beam, which fixed filter is arranged to block radiation with the wavelength of the radiation source and/or other than Raman emission received from the target or environment.

8. A method for optical measurement of a target, the method comprising:
providing a radiation beam to the target with Raman spectroscopy, receiving a measurement radiation beam of Raman scattered radiation including signature wavelengths of measured target material from the target and providing a signal which corresponds to the amount of radiation received by a detector from the target, and filtering the received measurement radiation beam with a Fabry-Perot interferometer, wherein:
a laser beam with a substantially fixed radiation wavelength is provided as the radiation beam,
the measurement radiation beam is detected with a single point detector,
the Fabry-Perot interferometer has a controllable pass band wavelength, the pass band wavelength of the Fabry-Perot interferometer is controlled sequentially into pass bands which correspond to signature wavelengths of the measured target material, the received measurement radiation signals of each measured signature wavelength are integrated, a measurement result is provided on the basis of the integrated signals, measurement radiation of a plurality of selected wavelengths is successively measured and cumulatively integrated, and the plurality of selected wavelengths and the integration times per each wavelength point are selected on the basis of the characteristic Raman spectrum of the target material to be measured.

9. The method according to claim 8, wherein the received measurement radiation signals are integrated as charges in the detector.

10. The method according to claim 8, wherein the radiation measurement signals of each signature are integrated separately.

11. The method according to claim 8, wherein only signatures of molecules which include a predetermined chemical element are measured.

12. The method according to claim 8, wherein the radiation with the wavelength of the radiation source and/or other than Raman emission received from the target or environment is blocked with a fixed filter.

13. The method according to claim 8, wherein the material contents of the target is monitored by continuously repeating the measurement sequence.

* * * * *